(12) United States Patent
Bocek et al.

(10) Patent No.: US 9,014,807 B2
(45) Date of Patent: Apr. 21, 2015

(54) LEAD FAULT DETECTION FOR IMPLANTABLE MEDICAL DEVICE

(75) Inventors: Joseph M. Bocek, Seattle, WA (US); Harley G. White, Fort Collins, CO (US); James O. Gilkerson, Stillwater, MN (US); John M. Link, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 10 days.

(21) Appl. No.: 13/297,785

(22) Filed: Nov. 16, 2011

(65) Prior Publication Data

US 2012/0158089 A1 Jun. 21, 2012

Related U.S. Application Data

(60) Provisional application No. 61/425,056, filed on Dec. 20, 2010.

(51) Int. Cl.
| | |
|---|---|
| *A61N 1/00* | (2006.01) |
| *A61N 1/37* | (2006.01) |
| *A61N 1/365* | (2006.01) |
| *A61N 1/08* | (2006.01) |

(52) U.S. Cl.
CPC ... *A61N 1/37* (2013.01); *A61N 1/00* (2013.01); *A61N 1/36521* (2013.01); *A61B 2560/0276* (2013.01); *A61N 2001/083* (2013.01)

(58) Field of Classification Search
CPC ............. A61N 1/00; A61N 1/02; A61N 1/04; A61N 1/05; A61N 1/08; A61N 1/18; A61N 1/36; A61N 1/37; A61N 1/365; A61N 1/368
See application file for complete search history.

(56) References Cited

U.S. PATENT DOCUMENTS

| | | | |
|---|---|---|---|
| 4,142,533 A | 3/1979 | Brownlee et al. | |
| 4,332,256 A | 6/1982 | Brownlee et al. | |

(Continued)

FOREIGN PATENT DOCUMENTS

| | | |
|---|---|---|
| EP | 0170365 A2 | 2/1986 |
| EP | 0384430 A2 | 8/1990 |
| EP | 0824936 A1 | 2/1998 |
| WO | WO-98/23327 A1 | 6/1998 |
| WO | WO-2012/003124 A2 | 1/2012 |

OTHER PUBLICATIONS

Berdyshev, S, et al., "Intracardiac Impedance as a Method for Ventricular Volume Monitoring—Investigation by a Finite-Element Model and Clinical Data", 2010 J. Phys.: Conf. Ser. 224 012095, (http://iopscience.iop.org/1742-6596/224/1/012095), (2010), 5 pgs.

(Continued)

*Primary Examiner* — Eric D. Bertram
*Assistant Examiner* — Elizabeth K So
(74) *Attorney, Agent, or Firm* — Schwegman Lundberg & Woessner, P.A.

(57) ABSTRACT

An implantable medical device can include a therapy circuit coupled to a therapy delivery terminal, the therapy circuit configured to generate a specified electrostimulation therapy for delivery to a tissue site via the therapy delivery terminal, and a measurement circuit for measuring at least two impedances of a first terminal combination including the therapy delivery terminal, the two impedances corresponding to at least two instances of excitation separated enough in time to capture an impedance artifact due at least in part to a motion of the heart, such as to determine an electrostimulation therapy lead status at least in part using the at least two impedances.

16 Claims, 6 Drawing Sheets

(56) References Cited

U.S. PATENT DOCUMENTS

| | | | |
|---|---|---|---|
| 4,595,009 | A | 6/1986 | Leinders |
| 4,785,812 | A | 11/1988 | Pihl et al. |
| 4,800,883 | A | 1/1989 | Winstrom |
| 4,821,723 | A | 4/1989 | Baker, Jr. et al. |
| 5,002,052 | A | 3/1991 | Haluska |
| 5,003,975 | A | 4/1991 | Hafelfinger et al. |
| 5,224,475 | A | 7/1993 | Berg et al. |
| 5,431,684 | A | 7/1995 | Archer et al. |
| 5,453,698 | A | 9/1995 | Williams et al. |
| 5,549,646 | A | 8/1996 | Katz et al. |
| 5,571,141 | A | 11/1996 | McNeil et al. |
| 5,571,156 | A | 11/1996 | Schmukler |
| 5,591,218 | A | 1/1997 | Jacobson |
| 5,626,619 | A | 5/1997 | Jacobsen et al. |
| 5,645,572 | A | 7/1997 | Kroll et al. |
| 5,755,742 | A | 5/1998 | Schuelke et al. |
| 5,891,179 | A | 4/1999 | Er et al. |
| 5,897,577 | A | 4/1999 | Cinbis et al. |
| 6,208,898 | B1 | 3/2001 | Gliner et al. |
| 6,493,586 | B1 | 12/2002 | Stahmann et al. |
| 6,643,545 | B2 | 11/2003 | Ideker et al. |
| 6,668,193 | B2 | 12/2003 | Ware et al. |
| 6,721,600 | B2 | 4/2004 | Jorgenson et al. |
| 7,047,083 | B2 | 5/2006 | Gunderson et al. |
| 7,050,851 | B2 | 5/2006 | Plombon et al. |
| 7,211,884 | B1 | 5/2007 | Davis et al. |
| 7,242,981 | B2 | 7/2007 | Ginggen |
| 7,283,863 | B2 | 10/2007 | Gunderson et al. |
| 7,289,851 | B2 | 10/2007 | Gunderson et al. |
| 7,369,898 | B1 | 5/2008 | Kroll et al. |
| 7,454,249 | B1 | 11/2008 | Bornzin et al. |
| 7,509,167 | B2 | 3/2009 | Stessman |
| 7,515,961 | B2 | 4/2009 | Germanson et al. |
| 7,522,957 | B2 | 4/2009 | Ostroff |
| 7,561,915 | B1 | 7/2009 | Cooke et al. |
| 7,574,259 | B1 | 8/2009 | Pei et al. |
| 7,623,930 | B2 | 11/2009 | Zeijlemaker et al. |
| 2002/0072769 | A1 | 6/2002 | Silvian et al. |
| 2002/0120307 | A1 | 8/2002 | Jorgenson et al. |
| 2002/0161406 | A1 | 10/2002 | Silvian |
| 2003/0088279 | A1 | 5/2003 | Rissmann et al. |
| 2003/0088282 | A1 | 5/2003 | Ostroff |
| 2004/0024424 | A1 | 2/2004 | Propp et al. |
| 2005/0107830 | A1 | 5/2005 | Huang |
| 2005/0288714 | A1 | 12/2005 | Ostroff |
| 2006/0167496 | A1 | 7/2006 | Nelson et al. |
| 2006/0253158 | A1 | 11/2006 | Stubbs et al. |
| 2006/0293591 | A1 | 12/2006 | Wahlstrand et al. |
| 2007/0293903 | A1 | 12/2007 | Bohn et al. |
| 2008/0114410 | A1* | 5/2008 | Ding et al. ............ 607/17 |
| 2008/0147132 | A1 | 6/2008 | Elahi et al. |
| 2009/0138058 | A1 | 5/2009 | Cooke et al. |
| 2009/0157132 | A1 | 6/2009 | Linder et al. |
| 2009/0157137 | A1 | 6/2009 | Gilkerson et al. |
| 2009/0157146 | A1 | 6/2009 | Linder et al. |
| 2009/0177110 | A1 | 7/2009 | Lyden et al. |
| 2009/0210021 | A1 | 8/2009 | Ostroff |
| 2009/0319014 | A1 | 12/2009 | Muecke et al. |
| 2010/0030286 | A1 | 2/2010 | Goetz et al. |
| 2011/0160808 | A1 | 6/2011 | Lyden et al. |
| 2011/0224747 | A1 | 9/2011 | Maile et al. |
| 2012/0004694 | A1 | 1/2012 | Ludwig et al. |

OTHER PUBLICATIONS

Bernstein, Neil E, et al., "Right-sided implantation and subpectoral position are predisposing factors for fidelis lead fractures", Heart Rhythm, 6(5), Supplement, Abstract PO02-145, (May 2009), S192.

Calame, Susan, et al., "A Large Single Center Experience with Fidelis Lead Failure: Lower Impedance at Time of Lead Implantation Independently Associates with Lead Failure", Heart Rhythm, 6(5) Supplement, Abstract PO05-158, (May 2009), S385.

Ellenbogen, Kenneth A, et al., "Lead Integrity Alert Performance for Non-Sprint Fidelis® ICD Lead Fractures", Heart Rhythm, 6(5) Supplement, Abstract PO03-125, (May 2009), S248-S249.

Jain, Sandeep K, et al., "Intensified Remote Monitoring in Medtronic Fidelis Patients", Heart Rhythm, 6(5) Supplement, Abstract PO05-156, (May 2009), S384.

Krahn, Andrew D, et al., "Acceleration of Fidelis Failure Rate in the Canadian Heart Rhythm Society Device Advisories Committee Registry", Heart Rhythm, 6(5) Supplement, Abstract AB35-1, (May 2009), S74-S75.

Kreuz, Jens, et al., "Detailed Electrical Analysis of Lead Failures in a Small Scaled Right Ventricular Defibrillator Lead: Reality of Sprint Fidelis Medical Device Recalls in a Single Centre", Heart Rhythm, 6(5), Supplement, Abstract PO02-126, (May 2009), S185.

Lyne, Jonathan C, et al., "High failure rate of sprint fidelis defibrillator lead in young/ACHD patients: the Brompton & Harefield experience", Heart Rhythm, 6(5), Supplement, Abstract AB12-1, (May 2009), S23.

Morrison, Thomas B, et al., "Risk Factors for Fidelis and non-Fidelis Implantable Defibrillator Lead Failure", Heart Rhythm, 6(5) Supplement, Abstract AB39-4, (May 2009), S84-S85.

Nguyen, Bich Lien, "High Sensing Integrity Counter with a Sprint FidelisTM Defibrillation Lead and a Cardiac Contractility Modulation Device: False Indication of High Voltage Lead Failure", Heart Rhythm, 6(5) Supplement, Abstract PO02-166, (May 2009), S200.

Patel, Amisha S, et al., "Modification to Lead Integrity Alert Improves Performance", Heart Rhythm, 6(5) Supplement, Abstract PO06-131, (May 2009), S438.

"International Application Serial No. PCT/US2011/041414, International Search Report mailed Dec. 29, 2011", 6 pgs.

"International Application Serial No. PCT/US2011/041414, Invitation to Pay Additional Fees mailed Nov. 9, 2011", 8 pgs.

"International Application Serial No. PCT/US2011/041414, Written Opinion mailed Dec. 29, 2011", 13 pgs.

"U.S. Appl. No. 12/977,158, Non Final Office Action mailed Jul. 15, 2013", 8 pgs.

"U.S. Appl. No. 12/977,158, Non Final Office Action mailed Nov. 15, 2012", 7 pgs.

"U.S. Appl. No. 12/977,158, Response filed Apr. 26, 2013 to Non Final Office Action mailed Nov. 15, 2012", 11 pgs.

"U.S. Appl. No. 13/166,297, Advisory Action mailed Sep. 13, 2013", 3 pgs.

"U.S. Appl. No. 13/166,297, Final Office Action mailed Apr. 15, 2013", 8 pgs.

"U.S. Appl. No. 13/166,297, Non Final Office Action mailed Nov. 8, 2012", 9 pgs.

"U.S. Appl. No. 13/166,297, Notice of Allowance mailed Oct. 1, 2013", 8 pgs.

"U.S. Appl. No. 13/166,297, Response filed Sep. 4, 2013 to Final Office Action mailed Apr. 15, 2013", 12 pgs.

"U.S. Appl. No. 13/166,297, Response filed Mar. 8, 2013 to Non Final Office Action mailed Nov. 8, 2012", 11 pgs.

"Australian Application Serial No. 2011271590, First Examiner Report mailed Aug. 23, 2013", 6 pgs.

"International Application Serial No. PCT/US2011/041414, International Preliminary Report on Patentability mailed Jan. 17, 2013", 14 pgs.

* cited by examiner

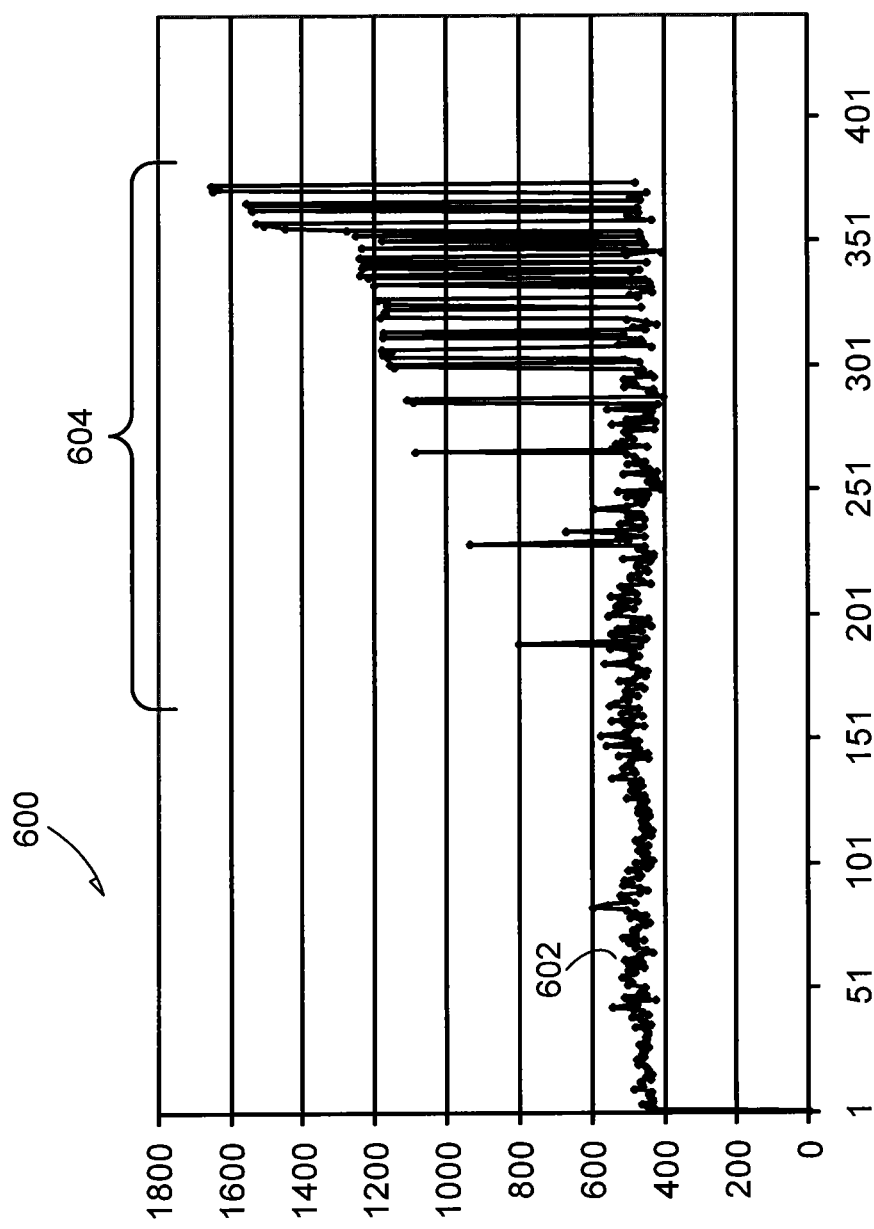

LEAD FAULT DETECTION FOR IMPLANTABLE MEDICAL DEVICE

CROSS REFERENCE TO RELATED APPLICATIONS

This application claims benefit of priority under 35 U.S.C. 119(e) to Bocek et al., U.S. Provisional Patent Application Ser. No. 61/425,056, entitled "Lead Fault Detection for implantable Medical Device", filed on Dec. 20, 2010.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among others.

Such IMDs can include electronic circuitry, such as to provide a desired electrostimulation, or to monitor physiologic activity. Such electronic circuitry can be coupled to an implantable lead assembly, such as including one or more electrodes or other electronic circuitry. A variety of different types of failures can affect systems including such IMDs and lead assemblies, such as including circuitry failures, electrical or mechanical coupling failures, or failure of a conductor or electrode included as a portion of a lead assembly attached to an IMD.

Germanson et al. (U.S. Pat. No. 7,515,961) mentions in vivo monitoring, detecting, and/or predicting potential failure modes or deleterious trends of chronically implanted medical electrical leads prior to actual failure of the leads, such as including using a relatively increased data sampling rate at various time intervals prior to actual detection of a deleterious trend.

Jorgenson et al. (U.S. Pat. Pub. No. 2002/0120307A1) mentions monitoring lead impedance, including collecting data from various sources in an implantable medical device system. Lead impedance, non-physiologic sensed events, percentage of time in mode switch, and results of capture management operation, sensed events, adversion pace counts, and refractory sense counts are used to determine a status of an implantable lead.

OVERVIEW

The present inventors have recognized, among other things, that IMDs can include or be coupled to one or more elongated conductors, such as a lead assembly carrying one or more distal electrostimulation or sensing electrodes contacting a desired tissue region of the patient. Some illustrative examples of IMDs that can include or be coupled to elongated electrical connections to the patient can include, but are not limited to, the following: (1) neuromodulators, such as deep brain stimulators (DBS), various pain control devices, or systems that can stimulate the spinal cord, muscle tissue, or other nerves of the body, e.g., a vagal nerve stimulator (VNS); (2) cardiac pacers; (3) automatic implantable cardioverter defibrillators (AICDs); (4) implantable diagnostic devices such as to monitor cardiac function, e.g., a loop recorder/Hotter-monitor-like recording device; or (5) cochlear implants. The present subject matter, such as described in detail herein, can be applied to these and other ambulatory devices such as other IMDs.

Such elongated lead assemblies including the one or more electrodes can fail unpredictably, possibly precluding delivery of an electrostimulation therapy or sensing of activity. Generally, in one approach, an impedance can be measured, such as once daily or weekly. The daily or weekly measurement can be compared to a range, such as including a fixed lower threshold and a fixed upper threshold. If a particular measurement is below the lower threshold, or above the upper threshold, an alert can be generated. However, lead faults can be transient, such as depending on environmental factors including temperature, posture, respiration, or cardiac motion, for example, among other factors.

The present inventors have recognized, among other things, that measuring one or more lead-related parameters more frequently can increase the likelihood of making a measurement at a particular time when a compromised lead exhibits an unexpected change in characteristic. Such lead-related parameters can include a lead impedance measurement, or an intrinsic amplitude measurement, for example.

The present inventors have also recognized, among other things, that lead impedance can be measured at multiple times during a cardiac cycle. For example, a lead impedance measurement can be made during or near a time of cardiac systole, and again during or near a time of cardiac diastole. In an example, such lead impedance measurements can be made every 50 milliseconds (ms), or according to one or more other repetition rates, durations, or sampling patterns. The present inventors have recognized, among other things, that lead impedance can be measured at least two times during a cardiac cycle, separated enough in time to capture an impedance artifact due to motion of the heart, such as due to an expansion or contraction of the heart. Such an approach can increase the likelihood of detecting a lead fracture or other lead failure that is elicited or exposed at least in part by the motion of the heart. It is believed that such a fault would not be as readily detected using a daily impedance measurement, or a lead impedance measurement made only once per cardiac cycle on an R-wave-synchronous basis.

An implantable medical device can include a therapy circuit coupled to a therapy delivery terminal, the therapy circuit configured to generate a specified electrostimulation therapy for delivery to a tissue site via the therapy delivery terminal, and a measurement circuit for measuring at least two impedances of a first terminal combination including the therapy delivery terminal, the two impedances corresponding to at least two instances of excitation separated enough in time to capture an impedance artifact due at least in part to a motion of the heart, such as to determine an electrostimulation therapy lead status at least in part using the at least two impedances.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5-6 include plots of illustrative examples of lead impedance including durations of intermittent variation in impedance measurements shown with respect to time.

DETAILED DESCRIPTION

Figure 1:
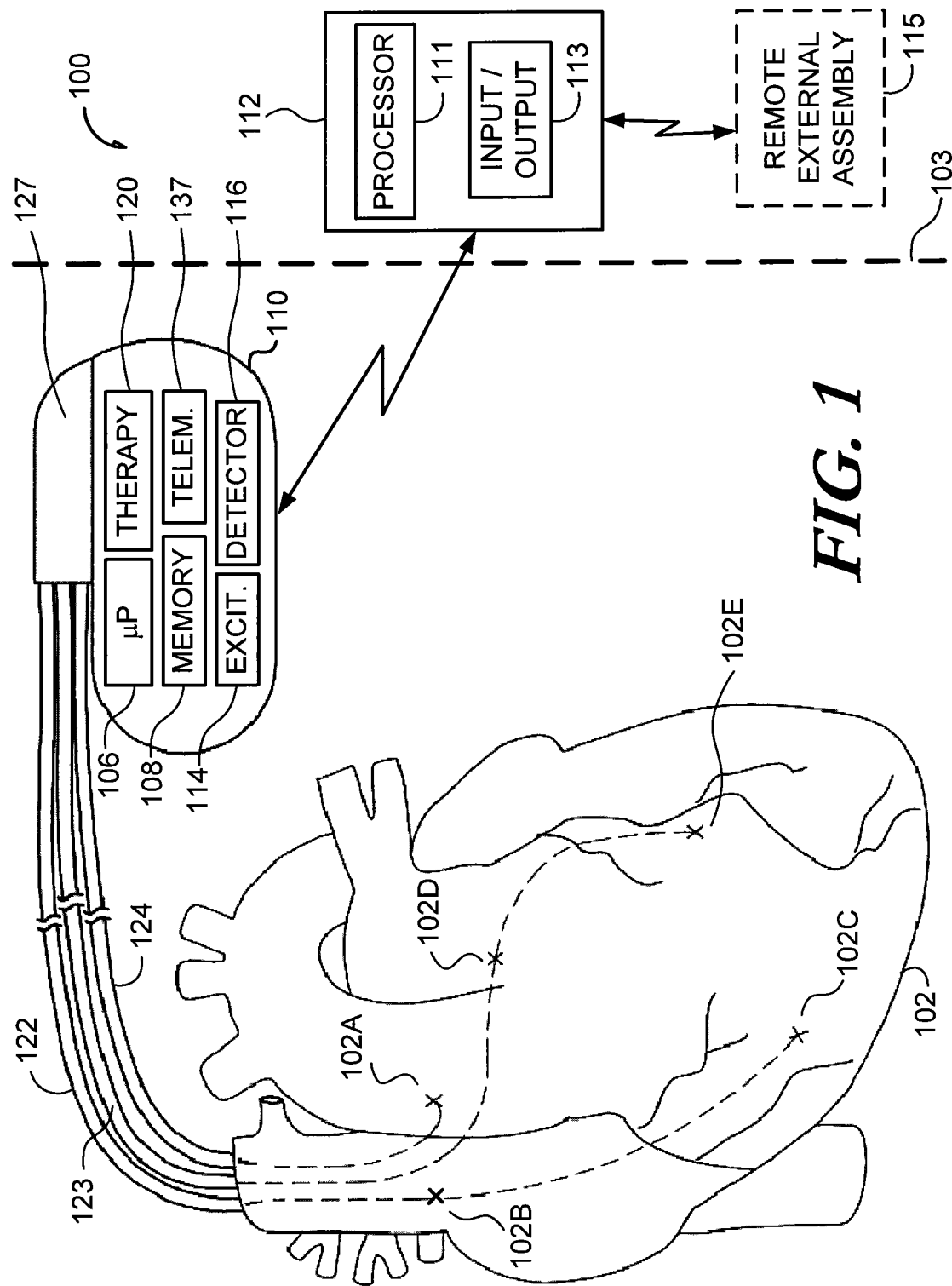
FIG. 1 illustrates generally an example of an apparatus that can include an implantable medical device, a local external assembly, or a remote external assembly.

FIG. 1 illustrates generally an example of an apparatus 100 that can include an implantable medical device (IMD) 110 or other ambulatory medical device, a local external assembly 112, or a remote external assembly 115. In the example of FIG. 1, the IMD 110 can include a microprocessor 106 or other processor circuit, such as coupled to a memory circuit 108. The microprocessor 106 can be configured to execute or interpret one or more instructions stored in the memory circuit 108, such as causing the IMD 110 to perform one or more techniques discussed in the examples of FIGS. 2-6.

In an example, the IMD 110 can include a therapy circuit 120, such as for generating or otherwise providing a desired or specified electrostimulation therapy for delivery to a tissue site such as a heart 102, such as via one or more implantable elongated lead assemblies. Such leads can include a first lead 122, such as intravascularly deliverable to an intracardiac location through the right atrium of the heart 102, to a right ventricle of the heart 102. For example, the first lead 122 can include one or more electrodes in superior vena cava region 10213, or in the right ventricular region 102C, such as to provide one or more of a bradycardia therapy (e.g., a pacing therapy), a tachyarrhythmia therapy (e.g., an anti-tachyarrhythmia pacing (ATP) therapy, a cardioversion therapy, or a defibrillation therapy). In an example, the IMD 110 can be coupled to a second lead 123, such as intravascularly deliverable to an intracardiac location in the right atrium of a heart 102. For example, the second lead 123 can include one or more electrodes in a right atrial region 102A of the heart 102, such as to provide one or more of an ATP therapy or a bradycardia therapy, among one or more other therapies. In an example, the IMD 110 can be coupled to a third lead 124, such as intravascularly deliverable through the heart 102 to venous location, such as within a great vein of the heart 102. The third lead 124 can include one or more electrodes, such as a tip electrode located at a distal region 102E, with respect to a conductive housing of the IMD 110, or including an electrode at a more proximal region 102D. One or more of the first, second or third leads 122-124 can be mechanically or electrically coupled to the 110 housing, such as a via a connector header 127 coupled to the housing of the IMD 110.

In an example, the first, second, or third leads 122-124 can include one or more internal conductors, such as one or more linear or coiled conductor shapes. Such conductors can fail, such as fracturing, separating, shorting out, becoming electrically "leaky." Various defects can include providing an unacceptably low impedance between conductors, or between a conductor and surrounding tissue (e.g., forming a "sneak path" back to the can), etc. Such failures can be transient or continuous. In an example, the IMD 110 can include an excitation circuit 114 that can be electrically coupled to one or more conductors included in one or more of the first-third leads 122-124, such as configured to provide one or more of a voltage or current excitation pulse to the conductor.

In an example, the IMD 110 can include a detector circuit 116 that can be configured to detect a voltage or current developed in response to the excitation provided by the excitation circuit 114. In an example, two lead impedances can be determined using information obtained from the excitation or detection circuits 114, 116, such as corresponding to two times during a cardiac cycle, the two times separated enough to capture an artifact (e.g., a change in impedance or other signature) due to a motion of the heart 102.

In an example, one or more trends can be determined, such as using information obtained about one or more lead impedance measurements, or one or more other measurements (e.g., an intrinsic event amplitude corresponding to a cardiac event sensed by the IMD 110). Such trends can include determining a short-term or long-term average, median, or other central tendency. Such trends can include one or more relative indications of information, such as a difference or ratio of information about a short-term or long-term trend, such as with respect to each other, or a relative indication of information about a presently-determined impedance measurement in comparison to one or more trends, such as illustrated in one or more of the illustrative pseudo code examples.

Such impedance or other information can be transferred to a local external assembly 112, such as a physician programmer, a bed-side monitor, a hand-held or personal communication device (e.g., a wireless assembly or cellular device), outside of a patient body 103, such as using a telemetry circuit 137. In an example, such information can be transferred, either wirelessly or via a wired network connection, to a remote external assembly 115, such as a server, a cellular communications or other wireless base station, a workstation accessible by a patient or caregiver, or one or more other remote assemblies.

In an example, one or more of the local external assembly 112 or the remote external assembly 115 can be used, such as to analyze one or more measurements made by the IMD 110, such as one or more of the lead impedance measurement or the intrinsic amplitude measurement, such as to determine a status of one or more of the leads 122-124. In an example, such as in response to one or more lead impedance measurements or intrinsic amplitude measurements, one or more of the IMD 110, the local external assembly 112, or the remote external assembly 115 can be used to trigger an increased measurement frequency or to trigger measurement of additional combinations of leads or electrodes, either via the intervention of a patient or caregiver, or automatically in response to one or more criteria such as discussed in the examples below.

Figure 2:
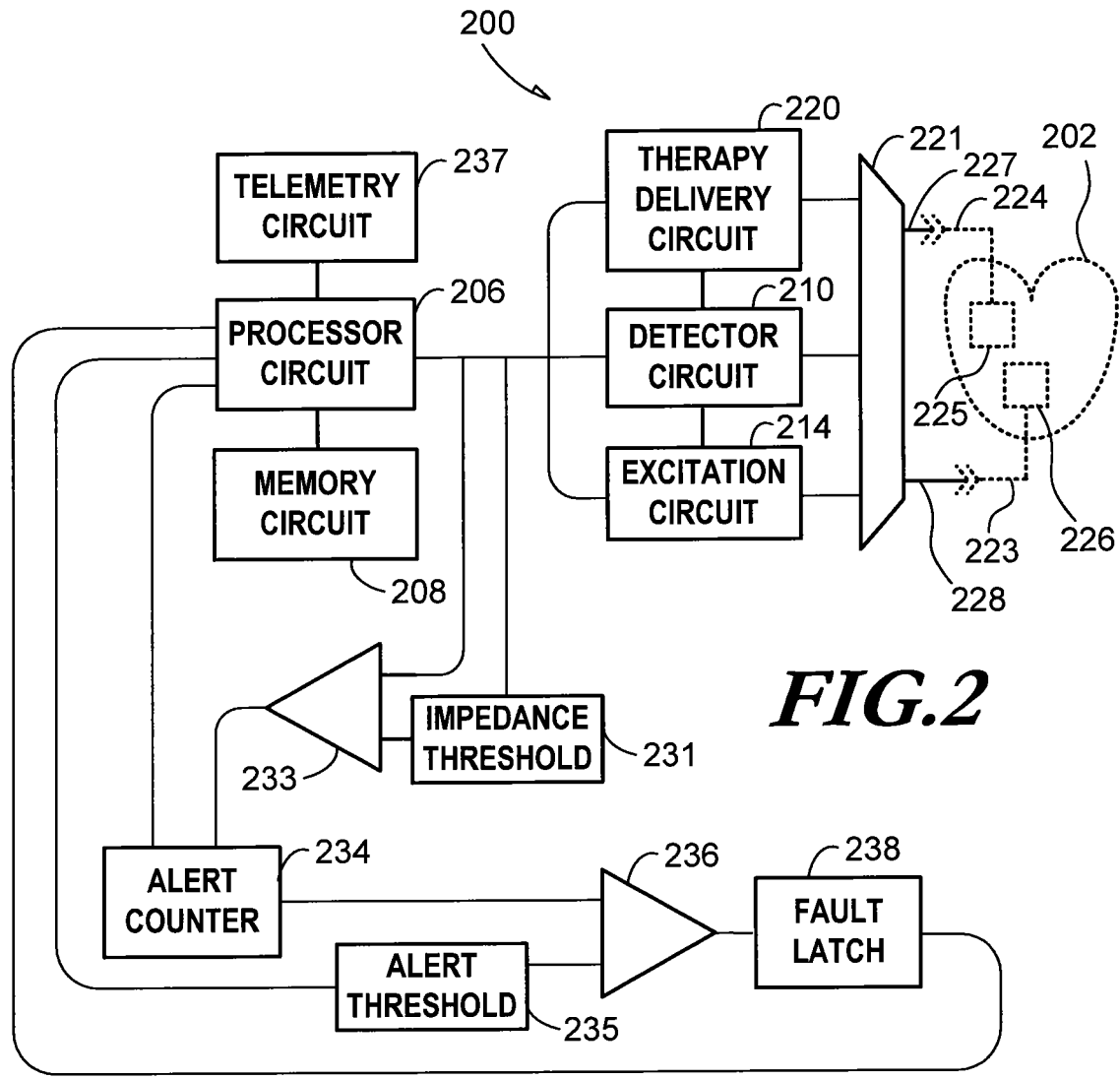
FIG. 2 illustrates generally an example of an apparatus that can include an implantable medical device.

FIG. 2 illustrates generally an example of an apparatus that can include an ambulatory medical device such as an IMD 200. Such an IMD 200 can include a therapy delivery circuit 220, such as coupled via a switch 221 to one or more therapy delivery terminals. In an example, such terminals can include a first therapy delivery terminal 227 that can be coupled to a first lead. 224, such as including a first electrode 225, or one or more other electrodes, such as disposed in or near a first tissue site to be electrostimulated a heart 202 or a neural target). In an example, the IMD 200 can include a second therapy delivery terminal 228 that can be coupled to a second lead 223, such as including a second electrode 226, such as located in or near a second tissue site e.g., the heart 202 or other target). For example, a first terminal combination can include the first therapy delivery terminal 227 and the second therapy delivery terminal 228, or one or more other terminals (e.g., a reference terminal or other non-therapy delivery terminal, such as located at or near a header or housing of the IMD 200).

In an example, the internal circuitry of IMD 200, such as shown in the example of FIG. 2, can include a combination of hardware and software. For example, one or more portions, elements, or circuits included in IMD 200 can be implemented, such as using an application-specific circuit constructed to perform one or more particular functions or a general-purpose circuit programmed to perform such function(s), such as according to one or more instructions stored in a memory circuit 208. Such a general-purpose circuit can be referred to generally as a processor circuit 206. Such a general-purpose circuit can include, but is not limited to, a microprocessor or a portion thereof, a microcontroller or portions thereof, and a programmable logic circuit or a portion thereof. For example, a "comparator" can include, among other things, an electronic circuit comparator constructed to perform the only function of a comparison between two signals or a portion of a general-purpose circuit driven by code instructing that portion of the general-purpose circuit to perform the comparison between the two signals. Similarly, a counter can be a digital circuit configured to measure a time duration or count a number of events or a portion of general-purpose circuit driven by code instructing that portion of the general-purpose circuit to perform a function such as including measuring a time duration or counting a number of events.

In the example of FIG. 2, a processor circuit 206 can be communicatively coupled to the therapy delivery circuit 220, such as to control or configure the therapy delivery circuit 220 to monitor activity at one or more tissue sites, or to deliver electrostimulation to the one or more tissue sites, such as to the first or second electrodes 225-226 via the respective first or second leads 224-223, such as corresponding to an electrode or lead configuration shown above in the examples of FIG. 1 or elsewhere.

As discussed in the example of FIG. 1, the IMD 200 can include an excitation circuit 214, such as configured to deliver one or more instances of non-therapeutic, non-tissue-stimulating voltage or current excitation to a desired terminal or combination of terminals, such as across the first or second terminals 227-228. In response, the IMD 200 can include a detector circuit, such as configured to receive corresponding voltages or currents developed at the first or second terminals 227-228 (or at another location, such as including a conductive housing of the IMD 200 or one or more other terminals). In an example, the excitation circuit 214 can be configured to provide multiple instances of excitation voltage or current within the duration of a cardiac cycle. Similarly, in an example, the detector circuit can be configured to obtain information about or receive corresponding voltages or currents corresponding to the multiple instances of excitation voltage or current, within the duration of the cardiac cycle.

In an example, an impedance measurement can be made, such as by injecting a current between the first terminal 227 and one or more other conductors, such as the housing of the IMD 200 or the second terminal 228, and measuring the voltage developed across the respective conductors. In an example, a synchronous current injection and voltage measurement can be used, such as discussed in relation to the physiologic impedance measurement techniques of U.S. patent application Ser. No. 12/350,728, entitled "IMPEDANCE MEASUREMENT AND DEMODULATION USING IMPLANTABLE DEVICE," filed on Jan. 8, 2009, assigned to Cardiac Pacemakers, Inc., which is herein incorporated by reference in its entirety, including its description of injecting one or more non-tissue-stimulating bi-phasic current pulses and synchronously measuring the voltage induced by the one or more bi-phasic current pulses.

In an example, the terminal combination need not include terminals that are all therapy delivery terminals. For example, a terminal combination under test can include one or more non-therapy delivery terminals, such as an indifferent electrode or other conductor such as located on or within a connector header of an implantable medical device, or elsewhere. Such an electrode combination can be used to determine an impedance corresponding to a path including at least one therapy delivery circuit terminal. In an example, the non-therapy delivery terminal can be a reference terminal (e.g., providing a reference potential for voltage measurement).

In an example, the processor circuit 206 can be configured to determine an impedance corresponding to the excited terminal combination, such as excited by the excitation circuit 214 and measured by the detection circuit 210. The processor circuit can be configured to determine at least two impedances corresponding to two respective instances of excitation and detection occurring within a cardiac cycle. For example, a first instance of excitation and detection can be used to determine a first impedance, such as corresponding to a portion of the cardiac cycle where the heart 202 is in or near a systolic condition. Similarly, a second instance of excitation and detection can be used to determine a second impedance, such as corresponding to a portion of the cardiac cycle where the heart 202 is in or near a diastolic condition. A fault can exist between the therapy delivery circuit 220 and the electrodes located in tissue, such as the first and second electrodes 225-226 located in or near the heart 202. If the fault is transient, determining the impedance during or near both systole and diastole may be more likely to capture an intermittent fault that depends on cardiac motion (e.g., a transient open or short that can be influenced by motion of the heart).

In an example, the IMD 200 can include one or more circuits such as to provide information about a cardiac cycle, such as including one or more of a mechanical or electrical sensing circuit. For example, an electrical sensing circuit can be included as a portion of one or more of the therapy delivery circuit 220 or the detector circuit 210, such as including one or more cardiac sensing amplifiers or analog-to-digital converters, for example. In an example, the IMD 200 can include sensing circuitry or interval detection circuitry such as shown and described in United States Patent Application No. 2008/0147132, Elahi et al., entitled "Method and Apparatus for Rate Accuracy Enhancement in Ventricular Tachycardia Detection," which is hereby incorporated herein by reference in its entire including its disclosure of sensing circuitry configured to sense atrial or ventricular electrograms indicative of cardiac electrical activity.

In an illustrative example, if a particular impedance measurement (e.g., a particular impedance determination made using information obtained from the detector circuit 210) indicates a lead impedance in violation of one or more rules outside of a specified range, above a specified threshold, or in violation of one or more criteria related to a short- or long-term trend), a frequency of one or more parameter determinations can be increased. For example, an impedance or intrinsic amplitude measurement can be made weekly or daily, such as compared by a first comparator 233 to a specified impedance threshold 231, or a specified impedance range (e.g., an absolute threshold, or an absolute range such as including a lower and an upper threshold). In the event of one or more daily or weekly impedance determinations falling outside the specified range, the comparator 233 can increment an alert counter 234, (e.g., declaring an alert). In an example, the alert counter can be coupled to the processor circuit 206 (or the processor circuit 206 can comprise the alert counter 234). For example, the processor circuit 206 can then control the excitation circuit 214 and the detector circuit 210, such as to more frequently measure intrinsic amplitude or impedance, such as to more likely detect an incipient or transient lead failure (e.g., as shown in the illustrative examples of impedance information of FIGS. 5-6). Such a frequency can be increased from a single daily or hourly impedance measurement to include instead using a burst of impedance measurements, such as separated in time by about 50 ms, or using one or more other patterns or repetition rates.

In an example, to increase a likelihood of detecting a lead fault or defect, white still conserving device power, a burst of multiple impedance measurements can be made, separated by an interval without such burst measurements. For example, such bursts can be delivered once a minute, or once an hour, or according to one or more other patterns or schedules, or as triggered by an alert. During the burst, the impedance measurements can occur rapidly, such as separated from each other by about 50 ms or some other duration, but such a burst can be limited to a total duration of one or just a few cardiac cycles, with such measurements suspended at other times (e.g., until another minute, hour, or other specified duration lapses), such as to conserve power.

In an example, the duration of one or more bursts of measurements or a separation between bursts can be adjusted automatically, or dynamically, such as depending on one or more of a patient activity level, respiration, a time of day, or one or more other factors. For example, a sedate or sleeping patient can be less likely to engage in activities that elicit a latent or incipient lead defect, so lead impedance determinations can be made less frequently during such times.

In an example, in addition to or instead of varying a frequency of impedance or intrinsic amplitude measurements, a wider variety of terminal combinations or "vectors" (e.g., combinations of terminals that can be coupled to various specified electrodes or lead conductors) can be measured, either routinely at specified intervals, or in response to an alert or one or more other criteria. For example, in a cardiac function management device, one or more of the following terminal combinations or "vectors" can be monitored, such as to provide additional diagnostic information to localize a faulty conductor, either automatically or with the aid of a caregiver reviewing one or more stored impedance determinations: (1) atrial tip relative to atrial ring (bipolar); (2) atrial tip relative to the IMD 200 housing (unipolar); (3) atrial ring relative to the IMD 200 housing (unipolar); (4) right ventricular tip relative to right ventricular ring (bipolar); (5) right ventricular tip relative to the IMD 200 housing (unipolar); (6) right ventricular ring relative to the IMD 200 housing (unipolar); (7) right ventricular tip relative to right ventricular coil (integrated bipolar); (8) right ventricular coil relative to the IMD 200 housing (unipolar); (9) right ventricular distal coil relative to right ventricular proximal coil; (10) right ventricular distal coil relative to the IMD 200 housing; (11) right ventricular proximal coil relative to the IMD 200 housing; (12) left ventricular tip relative to left ventricular ring (bipolar); (13) left ventricular tip relative to the IMD 200 housing (unipolar); (14) left ventricular ring relative to the IMD 200 housing (unipolar); (15) left ventricular tip relative to right ventricular ring (extended bipolar); or (16) left ventricular tip relative to right ventricular coil (extended bipolar).

In the example of FIG. 2, a count of a number of alerts provided by the alert counter 234 can be compared to an alert threshold 235 by a second comparator 236. In response, for example, a fault latch 238 can be set, such as coupled to the processor circuit 206 (e.g., declaring a fault). A fault can be more serious than an alert, such as indicating a persistent condition precluding or hindering delivery of electrostimulation therapy. In response to one or more of a fault or an alert, the processor circuit 206 can log other pertinent information about the patient or device (e.g., physiologic information), such as using the memory circuit 208, as discussed above. In an example, the IMD 200 can communicate with one or more of a local external assembly or a remote external assembly, such as using a telemetry circuit 237, such as to transmit information about one or more faults, alerts, or other information, or to provide one or more impedance determinations for similar analysis external to the patient. In an example, a determination of one or more of an alert or a fault can be made by one or more external assemblies, such as using lead impedance or other information obtained from the IMD 200.

In an example, other physiologic or IMD 200 information can be stored, such as corresponding to environmental or patient conditions at the time of one of one or more impedance determinations. For example, a change in lead 224-223 characteristics can be provoked by movement, such as by patient movement including exercise or deep breathing, or by changes in the mechanical position and size of the heart during pumping. Patient movement can move the lead at or near a housing of the IMD 200, such as including pectoral muscle movement. Similarly, a posture can alter the lead position. Pumping motion of the heart can move a region of the lead 224-223 that is distally-located with respect to a housing of the IMD 200.

Such movements (e.g., patient body, heart, or other motion) have the potential to expose lead 224-223 integrity issues. Thus, logging of such information (e.g., a respiration state, a posture, a patient activity level, cardiac electrograms, mechanical heart information such as pressure, etc.) during or near the time of a lead impedance measurement can aid in diagnosing a transient or incipient lead-related fault. Such logging can be triggered, for example, by a violation of one or more criteria including one or more fixed or dynamic thresholds or ranges, such as derived from a short- or long-term trend (e.g., a dynamic range or one or more dynamic limits determined using information about one or more previous impedance measurements or central tendencies). Such logging can include using information obtained from one or more sensors can be included as a portion of the such as an accelerometer, a posture sensor a multi-axis accelerometer), a respiration sensor e.g., an acoustic or impedance-based respiration sensor), a pressure sensor, a cardiac electrogram sensing channel, such as configured to provide stored or real-time electrograms, or information about an amplitude of intrinsic cardiac events.

In an example, information about a depth or other parameter of breathing (as compared to respiration rate or interval information) can be stored, such as corresponding to one or more lead status or lead impedance determinations, such as using one or more of the circuitry or techniques discussed in the previously-incorporated U.S. patent application Ser. No. 12/350,728.

In an example, an amplitude of excitation provided by the excitation circuit 214 can be adjusted, such as to provide excitation at an amplitude low or high enough to elicit non-linear behavior in the lead conductors or one or more connectors between the lead conductors and the circuitry of the IMD 200, such as a loose or corroded conductor, set-screw, spring clip, etc. For example, a lower-level millivolt-level range excitation can be used to determine an impedance, and compared to a higher-level volt-level range excitation. Similarly, in an example, a lower-level current excitation (e.g., microamps) can be used, along with a higher-level current excitation (e.g., hundreds of microamps). Such examples are illustrative, and one or more other ranges of excitation can be used, depending on the expected range of impedances to be measured. A relative indication of information about the lower- and higher-level measurements, such as a difference, ratio, or other indication can be used to determine a lead status. Similar results at both the tower and higher excitation level, such as both results within an acceptable range, can indicate an acceptable lead status. Differing impedance determination results between the lower-level and higher-level excitation can indicate corrosion, oxidation, an intermittent contact, or one or more other failure modes that might not be determined using a single-level impedance determination.

Figure 3:
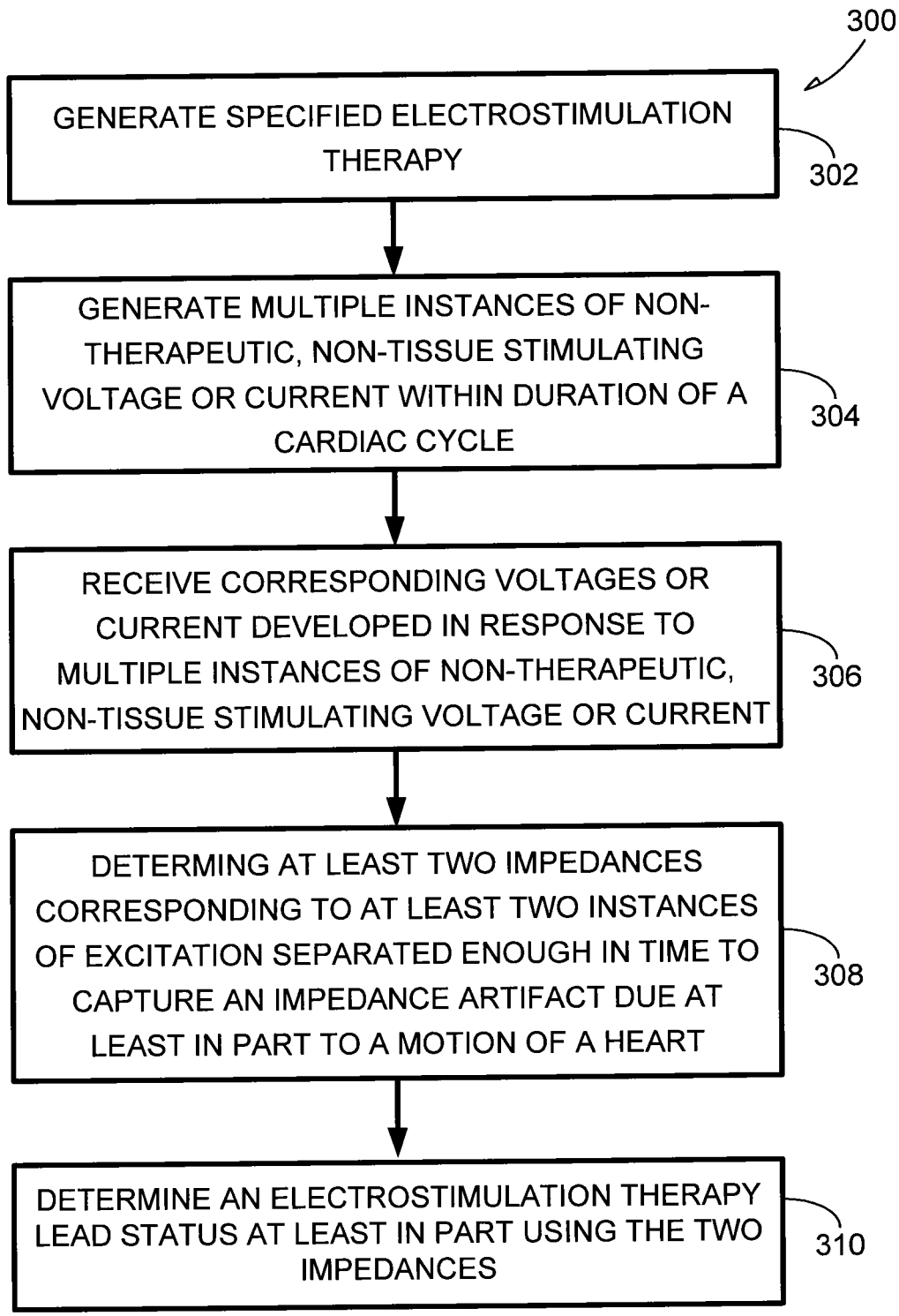
FIG. 3 illustrates generally a technique that can include determining an electrostimulation therapy lead status.

FIG. 3 illustrates generally a technique 300 that can include determining an electrostimulation therapy lead status, such as using one or more of the apparatus or techniques of FIGS. 1-2, such as for determining an electrostimulation therapy lead status. At 302, the technique 300 can include generating a specified electrostimulation therapy (e.g., a pacing therapy, a neural stimulation therapy, an antitachyarrhythmia therapy, etc.), such as using the therapy circuit of the examples of FIGS. 1-2. At 304, the technique 300 can include generating multiple instances of non-therapeutic, non-tissue stimulating voltage or current excitation, such as within a duration of a cardiac cycle, as discussed in the examples of FIGS. 1-2.

At 306, the techniques can include obtaining or receiving information about a corresponding voltage or current developed in response to the multiple instances of non-therapeutic, non-tissue stimulating voltage or current. At 308, the technique 300 can include determining at least two impedances corresponding to at least two instances of excitation separated enough in time to capture an impedance artifact due at least in part to a motion of a heart, as discussed in the examples of FIGS. 1-2. At 310, the technique can include determining an electrostimulation therapy lead status at least in part using information about the two impedances.

The pseudo code examples include techniques comprising various checks and related criteria that can be used for evaluating one or more of an implantable lead impedance, an intrinsic sensed event amplitude, a pacing threshold, or one or more other parameters. Such evaluation can include a short-term shift check, a long-term shift check, a day-to-day variability check, a daily absolute range check, and an outlier check. In an example, such techniques as discussed above or shown in the pseudo code examples can be used for determining an electrostimulation therapy lead status, such as using apparatus or techniques as discussed above in the examples of FIGS. 1-3, such as to detect the impedance or other signatures corresponding to the illustrative examples of FIGS. 4-6. For example, one or more of the thresholds or ranges included in the pseudo code examples be set to a specified or desired level, such as to tailor the check to a particular lead configuration, or range of expected ambulatory impedances, or to adjust a sensitivity or specificity of fault detection. For example, one or more of the thresholds or ranges can be specified or established, such as using information acquired from a population of patients, devices, or leads, or various combinations thereof, such as using information about both normally-functioning combinations and combinations that have exhibited clinically-unacceptable performance. For example, such information can be obtained using one or more of the local or external assemblies 112 or 115, such as remotely without requiring explants or without requiring return of failed apparatus from the field.

In an example, a failure of one or more of the checks, such as included in the pseudo code examples, can be used to increment an alert counter, such as shown in the example of FIG. 2. In an example, multiple days' (or other specified intervals') data can be evaluated before declaring a lead fault, such as using the alert threshold as shown in the example of FIG. 2, or using one or more other criteria. For example, if "X" days out of a consecutive "Y" days indicate a lead alert, according to one or more criteria related to the examples above or in the pseudo code examples, then a fault can be declared. For example, a 2-consecutive-day criterion (e.g., an alert generated or declared two consecutive days) can be used, or a "3 of 4" criterion (e.g., an alert generated or declared in 3 out of 4 of the previous days, either consecutively or non-consecutively).

In an example, if the measurements for determining a lead status include using pacing thresholds or measurement of intrinsic events, such measurements should be disregarded if the underlying heart rhythm is arrhythmic, such as to avoid confounding the lead status determination.

In one approach, outliers can be discarded to improve specificity (e.g., single samples deviating from the rest of the population in excess of a relative or absolute amount). The present inventors have recognized that transient lead defects or faults can produce outliers, and that merely discarding such information may preclude detection of certain faults. In an example, instead of discarding outliers, one or more of the apparatus or techniques of FIGS. 1-3 can be used, such as to count a number of outliers during a specified interval (e.g., over a period of a day, a week, a month, or one or more other intervals). If a count of outliers exceeds a specified threshold, an alert can be declared. A measurement (e.g., an impedance determination) can be classified as an outlier such as if a difference or ratio between the measurement and one or more central tendencies of previous measurement exceeds a specified threshold. Such central tendencies can include one or more of an average, a median, etc., such as shown in the pseudo code examples or elsewhere.

In an example, in addition or instead of the outlier check above, a second outlier check can be performed. In such a second outlier check, a difference or other relative indication of a present impedance measurement can be determined with respect to a central tendency of impedance information (e.g., a median, an average, etc.) Then, the difference or relative indication of the present impedance determination can be compared to an indication of spread or variability in the previous impedance determinations. In an illustrative example, a present impedance determination can trigger an alert if its difference from the median of previous impedance determinations exceeds an estimated standard deviation of previous lead impedance measurements by three times or more. Other thresholds can be used, and the duration over which the central tendency or indication of spread are determined can be specified (e.g., 7 days, as in the illustrative pseudo code examples).

Figure 4:
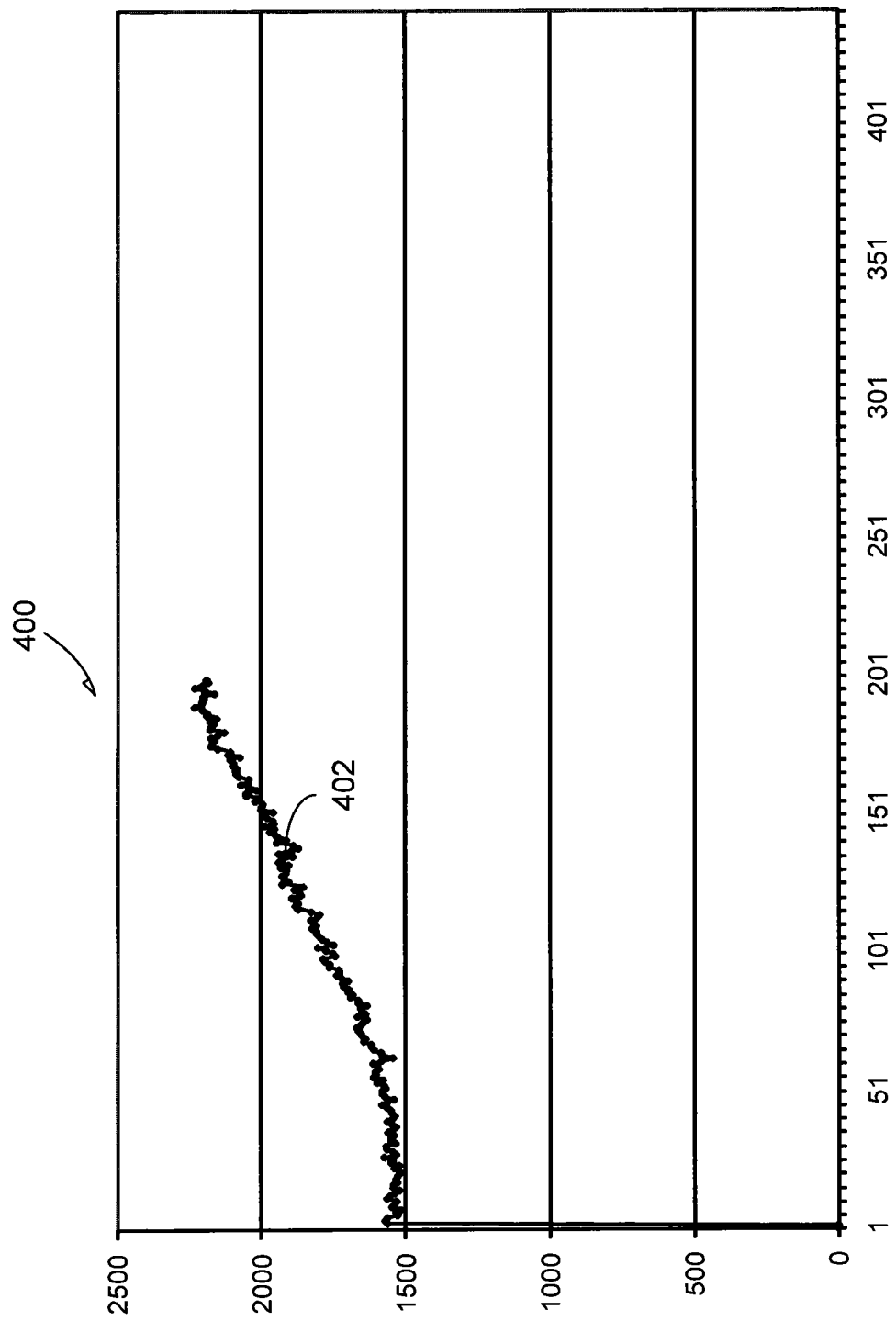
FIG. 4 includes a plot of an illustrative example of a lead impedance including a gradual increase in impedance measurements shown with respect to time.

FIG. 4 includes a plot of an illustrative example 400 of a lead impedance including a gradual increase shown with respect to time. In this illustrative example, a lead impedance 402 can initially be stable, such as over the duration shown corresponding to the first 50 samples. Then, the lead impedance 402 gradually increases, such as eventually exceeding a fixed threshold of 2000 ohms. In an example, if the horizontal axis is a sample number, corresponding to a result of a daily measurement, the illustrative example of FIG. 4 might take over 150 days to register a failing lead impedance measurement (e.g., exceeding a fixed threshold of 2000 ohms). In an example, a slope or difference between successive measurements can be used at least in part as a lead status criterion, such as to detect a change from the relatively stable initial duration of the lead impedance 402, to an increasing impedance 402.

Figure 5:
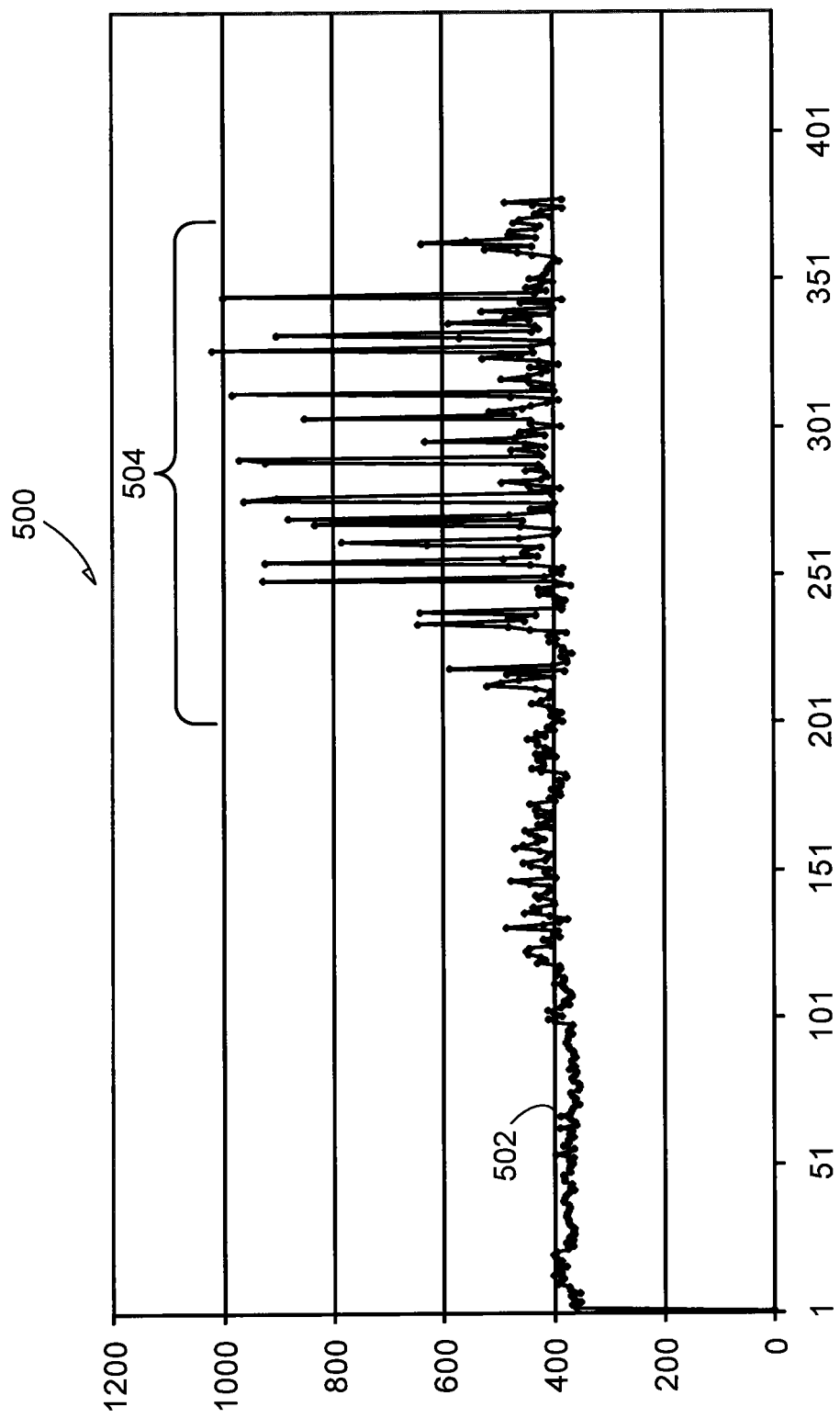

FIGS. 5-6 include plots of illustrative examples 500, 600 of lead impedance 502, 602 including durations of intermittent variation 504, 604 shown with respect to time. It is believed that one or more of an outlier check, a day-to-day variability check, an increased measurement frequency, a short-term check, or other criteria or techniques might be used, such as discussed in the examples of FIGS. 1-3, such as to detect the intermittent behavior shown in the illustrative examples of FIGS. 5-6, even though such impedance data might not exceed an absolute threshold. For example, such relative criteria or an increased measurement frequency might be used to detect a change in an electrostimulation lead therapy status earlier than using an absolute threshold.

Various Examples and Notes

Example 1 includes subject matter, such as an apparatus, comprising an implantable medical device including a therapy circuit coupled to a therapy delivery terminal, the therapy circuit configured to generate a specified electrostimulation therapy for delivery to a tissue site via the therapy delivery terminal, a measurement circuit comprising an excitation circuit, configured to generate multiple instances of a non-therapeutic, non-tissue-stimulating voltage or current excitation using a first terminal combination including the therapy delivery terminal, within the duration of a cardiac cycle and a detector circuit, configured to receive corresponding voltages or currents developed at the first terminal combination in response to the multiple instances of excitation, within the duration of the cardiac cycle. In Example 1, the implantable medical device includes a processor circuit, configured to determine at least two impedances using information about the instances of excitation, and information provided by the measurement circuit about the received voltages or currents, the two impedances corresponding to at least two instances of excitation separated enough in time to capture an impedance artifact due at least in part to a motion of the heart, the processor circuit configured to determine an electrostimulation therapy lead status at least in part using the at least two impedances.

In Example 2, the subject matter of Example 1 can optionally include an excitation circuit is configured to generate a current excitation at the first terminal combination, and a detector configured receive a voltage developed at the first terminal combination in response to the current excitation.

In Example 3, the subject matter of one or any combination of Examples 1-2 can optionally include an excitation circuit configured to inject a pulsed current excitation into the first terminal combination, the first terminal combination comprising a reference terminal, and a detector circuit configured to measure a voltage developed across the first terminal combination.

In Example 4, the subject matter of one or any combination of Examples 1-3 can optionally include an excitation circuit configured to generate a voltage excitation across the first terminal combination, and a detector circuit configured to receive a current developed at the first terminal combination in response to the voltage excitation.

In Example 5, the subject matter of one or any combination of Examples 1-4 can optionally include an implantable lead, including an implantable electrode, the implantable lead providing an electrical coupling between a terminal included in the first terminal combination and the electrode.

In Example 6, the subject matter of one or any combination of Examples 1-5 can optionally include a first comparator configured to compare an impedance determined by ate processor against a specified range, and a processor configured to declare an alert, in response, if the impedance falls outside the specified range.

In Example 7, the subject matter of one or any combination of Examples 1-6 can optionally include a specified range determined using information about one or more previously-determined impedances.

In Example 8, the subject matter of one or any combination of Examples 1-7 can optionally include a specified range including an upper threshold and a lower threshold, one or more of the upper or lower thresholds adjusted using an adjusted threshold specified relative to a central tendency of previously-determined impedances.

In Example 9, the subject matter of one or any combination of Examples 1-8 can optionally include a specified range determined using information about the type or location of an implantable lead, the lead including the electrode coupled to the terminal included in the first terminal combination.

In Example 10, the subject matter of one or any combination of Examples 1-9 can optionally include a processor circuit configured to adjust the interval between successive instances of excitation.

Example 11, the subject matter of one or any combination of Examples 1-10 can optionally include a processor circuit configured to decrease the interval between successive instances of excitation in response to a declared alert.

In Example 12, the subject matter of one or any combination of Examples 1-11 can optionally include a processor circuit configured to count a number of alerts, the apparatus including a second comparator configured to compare a count of the number of alerts against a specified threshold, and the processor circuit configured to declare a lead fault, in response, when the count of the number of alerts exceeds the specified threshold.

In Example 13, the subject matter of one or any combination of Examples 1-12 can optionally include an external assembly, the implantable medical device including a telemetry circuit configured to transfer information, between the implantable medical device and the external assembly, about one or more instances of the measurement circuit excitation, the received voltage or current, the determined impedance, a count of declared alerts, or a lead status indicative of a lead fault.

In Example 14, the subject matter of one or any combination of Examples 1-13 can optionally include a processor circuit configured to adjust the electrostimulation electrode configuration or one or more electrostimulation parameters to be used by the therapy circuit for providing subsequent electrostimulation, in response to information about the alert.

In Example 15, the subject matter of one or any combination of Examples 1-14 can optionally include a processor circuit configured to select a second terminal combination for use in providing subsequent electrostimulation in response to an alert declared in relation to an impedance determined at least in part using the first terminal combination.

In Example 16, the subject matter of one or any combination of Examples 1-15 can optionally include a processor circuit configured to determine a relative indication of information between at least two impedances corresponding to at least two excitation instances provided by the measurement circuit within an interval of a single cardiac cycle, the apparatus including a comparator configured to compare the relative indication of information to a threshold, and the processor circuit configured to declare an alert, in response, if the relative indication of information exceeds the threshold.

Example 17 can include, or can optionally be combined with the subject matter of one or any combination of Examples 1-16 to include, subject matter (such as a method, a means for performing acts, or a machine-readable medium including instructions that, when performed by the machine, cause the machine to perform acts) comprising generating a specified electrostimulation therapy for delivery to a tissue site via a therapy delivery terminal of the implantable medical device, generating multiple instances of a non-therapeutic, non-tissue-stimulating voltage or current excitation at a first terminal combination including the therapy delivery terminal, within the duration of a cardiac cycle, receiving corresponding voltages or currents developed at the first terminal combination in response to the multiple instances of non-therapeutic, non-tissue-stimulating excitation, within the duration of the cardiac cycle, determining at least two impedances using information about the instances of non-therapeutic, non-tissue-stimulating excitation, and the information about the received voltages or currents, the two impedances corresponding to at least two instances of excitation separated enough in time to capture an impedance artifact due at least in part to a motion of the heart, and determining an electrostimulation therapy lead status at least in part using the two impedances.

In Example 18, the subject matter of Example 17 can optionally include multiple instances of non-therapeutic, non-tissue-stimulating excitation comprising a voltage excitation generated across the first terminal combination, and the receiving the corresponding voltages or currents including receiving a current developed at the first terminal combination in response to the non-therapeutic, non-tissue-stimulating excitation.

In Example 19, the subject matter of one or any combination of Examples 17-18 can optionally include multiple instances of non-therapeutic, non-tissue-stimulating excitation comprising a current excitation injected into the first terminal combination, and the receiving the corresponding voltages or currents including receiving a voltage developed across the first terminal combination in response to the non-therapeutic, non-tissue-stimulating excitation.

Example 20, the subject matter of one or any combination of Examples 17-19 can optionally include comparing a determined impedance against a specified range, and, in response, declaring an alert if the impedance falls outside the specified range.

In Example 21, the subject matter of one or any combination of Examples 17-20 can optionally include determining the specified range using information about one or more previously-determined impedances.

In Example 22, the subject matter of one or any combination of Examples 17-21 can optionally include a specified range including an upper threshold and a lower threshold, and determining the specified range including instructions to adjust one or more of the upper or lower thresholds using an adjusted threshold specified relative to a central tendency of previously-determined impedances.

In Example 23, the subject matter of one or any combination of Examples 17-22 can optionally include determining the specified range including using information about the type or location of an implantable lead, the lead including the electrode coupled to a therapy delivery terminal included in the first terminal combination.

In Example 24, the subject matter of one or any combination of Examples 17-23 can optionally include adjusting the interval between successive instances of excitation.

In Example 25, the subject matter of one or any combination of Examples 17-24 can optionally include decreasing the interval between successive instances of excitation in response to a declared alert.

Example 26, the subject matter of one or any combination of Examples 17-25 can optionally include counting a number of alerts, comparing a count of the number of alerts against a specified threshold, and, in response, declaring a lead fault when the count of the number of alerts exceeds the specified threshold.

In Example 27, the subject matter of one or any combination of Examples 17-26 can optionally include adjusting the electrostimulation electrode configuration or one or more electrostimulation parameters to be used by a therapy circuit for providing subsequent electrostimulation, in response to information about the alert.

In Example 28, the subject matter of one or any combination of Examples 17-27 can optionally include selecting a second terminal combination for use in providing subsequent electrostimulation in response to an alert declared in relation to an impedance determined at least in part using the first terminal combination.

In Example 29, the subject matter of one or any combination of Examples 17-28 can optionally include determining a relative indication of information between at least two impedances corresponding to at least two excitation instances provided by the measurement circuit within an interval of a single cardiac cycle, and comparing the relative indication of information to a threshold, and, in response, declaring an alert if the relative indication of information exceeds the threshold.

Example 30 includes subject matter (such as an apparatus) comprising an implantable medical device including a processor and a memory circuit, the implantable medical device comprising a means of generating a specified electrostimulation therapy for delivery to a tissue site via an implantable electrode coupled to a first terminal combination of the implantable medical device, a means of generating multiple instances of a non-therapeutic, non-tissue-stimulating voltage or current excitation at the first terminal combination, over the duration of a cardiac cycle, a means of receiving corresponding voltages or currents developed at the first terminal combination in response to the multiple instances of non-therapeutic, non-tissue-stimulating excitation, over the duration of the cardiac cycle, the processor circuit configured to determine at least two impedances using information about the instances of non-therapeutic, non-tissue-stimulating excitation, and the information about the received voltages or currents.

These examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples," Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof, or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more," in this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein," Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Illustrative Examples in Pseudo Code

```
For each Leadtype {RV,RA,LV}
\\ For example, check daily measurements for each lead for days for which measurements are
available up to last 180 days.
\\ Short Term Shift Check Illustrative Example
\\ Check for short term changes for each day vs. a median average of N previous days (e.g. 7 days).
        For lead Meastype {Impedance, Amplitude, Pace Threshold},
                For each day, compute median average of last N days (e.g. 7 days).
                        Compute difference of current day to median average.
                IF
                        (difference >
                        LeadtypeFaultThresShortTermAbsoluteMeastypeIncrease
                        AND
                        ratio of difference to median average >
                        LeadtypeFaultThresShortTermRelativeMeastypeIncrease)
                OR
                        (difference < LeadFaultThresShortTermAbsoluteMeastypeDecrease
                        AND
                        ratio of difference to median average <
                        LeadFaultThresShortTermRelativeMeastypeDecrease)
                THEN declare a possible Leadtype alert for this day.
\\ End Short Term Shift Check
\\Long Term Shift Check Illustrative Example
\\ Check absolute and relative shift of a long term period of M days (e.g. 60 days)
        For each day for which N + M days of previous measurements are available:
                For each lead Meastype {Impedance, Amplitude, Pace Threshold}
                        Compute difference median averages of last N days (e.g. 7 days) for two
                        epochs spaced apart by M days (e.g. 60 days).
                        IF
                                (difference >
                                LeadtypeFaultThresLongTermAbsoluteMeastypeIncrease
                                AND
                                ratio of difference to average of median averages >
                                LeadtypeFaultThresLongTermRelativeMeastypeIncrease)
                        OR
                                (difference <
                                LeadtypeFaultThresLongTermAbsoluteMeastypeDecrease
                                AND
                                ratio of difference to average of median averages <
                                LeadtypeFaultThresLongTermRelativeMeastypeDecrease)
                        THEN declare a possible a possible Leadtype alert for this day.
```

-continued

```
\\ End Long Term Shift Check
\\Day to Day Variability Check Illustrative Example
\\ Check Absolute and Relative Variability over an epoch of M days (e.g. 10 days)
    For each day for which M days of previous data are available.
        For each Meastype (Impedance, Amplitude, Pace Threshold):
            Compute Variability of lead measurements as the sum of absolute
            differences between consecutive daily measurements.
            IF
                Variability > LeadFaultThresVariabilityAbsoluteMeas
                AND
                ratio of Variability to mean of measurements >
                LeadFaultThresVariabilityRelativeMeas
            THEN declare a possible Leadtype alert.
\\ End Day to Day Variability Check
\\Outlier Check Illustrative Example
\\ Check for outliers each day vs. a median average of N previous days (e.g. 7 days),
    For lead Meastype {Impedance, Amplitude, Pace Threshold}.
        For each day. compute median average of last N days (e.g. 7 days).
            Compute ratio of current day to median average.
            IF
                (Ratio> LeadtypeFaultRatioOutlierMeastypeIncrease
                OR
                (Ratio < LeadtypeFaultRatioOutlierMeastypeDecrease
            THEN classify measured value as an outlier
    For measurement declared as an outlier,
        Record date/time of outlier for the given measurement type
        Count all outliers within the last month and all measurements within the last month
        IF
            OutlierCount/MeasurementCount >
            LeadtypeFaultMaxOutlierRatioMeastype
        THEN declare a possible Leadtype alert for this day.
\\ End Outlier Check
\\Outlier Check vs. Previous Variability Illustrative Example
\\ Check for outliers each day vs. a median average of N previous days (e.g. 7 days),
  For lead Meastype {Impedance, Amplitude, Pace Threshold}.
    For each day. compute median average and standard deviation of last N days (e.g. 20 days).
            Compute ratio of (current day – median average)/standard deviation
            IF
                (Ratio> LeadtypeFaultRatioOutlierVariabilityMeastypeIncrease
                OR
                (Ratio < LeadtypeFaultRatioOutlierVariabilityMeastypeDecrease
            THEN classify measured value as an outlier
    For measurement declared as an outlier,
        Record date/time of outlier for the given measurement type
        Count all outliers within the last month and all measurements within the
        last month.
        IF
            OutlierCount/MeasurementCount >
            LeadtypeFaultMaxOutlierRatioMeastype
        THEN declare a possible Leadtype alert for this day.
\\ End Outlier Check
\\Daily Absolute Range Check Illustrative Example
\\ Check Daily Values for each measurement type against high and low range limits
    For each day for which data is available:
        For each Meastype (Impedance, Amplitude, Pace Threshold):
            IF daily value> LeadFaultThresholdUpperRange Value
            OR
            daily value < LeadFaultThresholdLowerRangeValue
            THEN declare a possible Leadtype alert for this day.
\\ End Daily Absolute Range Check
Check all days for which data was evaluated for this Leadtype.
If there is a lead type alert on the most recent day evaluated OR there are X of Y consecutive days
with lead type alerts, then declare a possible Leadtype Fault
Alert (display "Needs Evaluation" on lead type check.
\\ End Leadtype Check
```

The claimed invention is:

1. An apparatus, comprising:
an implantable medical device, comprising:
a therapy circuit coupled to a therapy delivery terminal, the therapy circuit configured to generate a specified electrostimulation therapy for delivery to a tissue site via the therapy delivery terminal;
a measurement circuit comprising:
an excitation circuit, configured to generate multiple instances of a non-therapeutic, non-tissue-stimulating voltage or current excitation using a first terminal combination including the therapy delivery terminal, within the duration of a cardiac cycle; and
a detector circuit, configured to receive corresponding voltages or currents developed at the first terminal combination in response to the multiple instances of excitation, within the duration of the cardiac cycle; and a processor circuit coupled to the measurement circuit and configured to determine at least two impedances using information about the instances of excitation, and information provided by the measurement circuit about the received voltages or currents, the two impedances corresponding to at least two instances of excitation separated enough in time to capture an impedance artifact indicative of a status of an electrostimulation therapy lead, the impedance artifact elicited at least in part by a motion of the heart;

wherein the processor circuit is configured to determine the electrostimulation therapy lead status at least in part using the at least two impedances.

2. The apparatus of claim 1, wherein the excitation circuit is configured to generate a current excitation at the first terminal combination; and wherein the detector is configured receive a voltage developed at the first terminal combination in response to the current excitation.

3. The apparatus of claim 2, wherein the excitation circuit is configured to inject a pulsed current excitation into the first terminal combination, the first terminal combination comprising a reference terminal; and wherein the detector circuit is configured to measure a voltage developed across the first terminal combination.

4. The apparatus of claim 1, wherein the excitation circuit is configured to generate a voltage excitation across the first terminal combination; and wherein the detector circuit is configured to receive a current developed at the first terminal combination in response to the voltage excitation.

5. The apparatus of claim 1, further comprising an implantable lead, including an implantable electrode, the implantable lead providing an electrical coupling between a terminal included in the first terminal combination and the electrode.

6. The apparatus of claim 1, comprising a first comparator configured to compare an impedance determined by the processor circuit against a specified range; and in response, wherein the processor circuit is configured to declare an alert if the impedance falls outside the specified range.

7. The apparatus of claim 6, wherein the specified range is determined using information about one or more previously-determined impedances.

8. The apparatus of claim 6, wherein the specified range includes an upper threshold and a lower threshold; and wherein one or more of the upper or lower thresholds are adjusted using an adjusted threshold specified relative to a central tendency of previously-determined impedances.

9. The apparatus of claim 6, wherein the specified range is determined using information about the type or location of an implantable lead, the lead including the electrode coupled to the terminal included in the first terminal combination.

10. The apparatus of claim 6, wherein the processor circuit is configured to adjust the interval between successive instances of excitation.

11. The apparatus of claim 10, wherein the processor circuit is configured to decrease the interval between successive instances of excitation in response to a declared alert.

12. The apparatus of claim 6, wherein the processor circuit is configured to count a number of alerts; and wherein the apparatus comprises a second comparator configured to compare a count of the number of alerts against a specified threshold; and in response, wherein the processor circuit is configured to declare a lead fault when the count of the number of alerts exceeds the specified threshold.

13. The apparatus of claim 6, further comprising an external assembly; and wherein the implantable medical device comprises a telemetry circuit configured to transfer information, between the implantable medical device and the external assembly, about one or more instances of the measurement circuit excitation, the received voltage or current, the determined impedance, a count of declared alerts, or a lead status indicative of a lead fault.

14. The apparatus of claim 6, wherein the processor circuit is configured to adjust the electrostimulation electrode configuration or one or more electrostimulation parameters to be used by the therapy circuit for providing subsequent electrostimulation, in response to information about the alert.

15. The apparatus of claim 6, wherein the processor circuit is configured to select a second terminal combination for use in providing subsequent electrostimulation in response to an alert declared in relation to an impedance determine at least in part using the first terminal combination.

16. The apparatus of claim 1, wherein the processor circuit is configured to determine a relative indication of information between at least two impedances corresponding to at least two excitation instances provided by the measurement circuit within an interval of a single cardiac cycle;

wherein the apparatus includes a comparator configured to compare the relative indication of information to a threshold; and wherein the processor circuit is configure to declare an alert, in response, if the relative indication of information exceeds the threshold.

* * * * *